United States Patent [19]
Lau et al.

[11] Patent Number: 5,091,291
[45] Date of Patent: Feb. 25, 1992

[54] ALKYL SUBSTITUTED PHOTOGRAPHIC COUPLERS AND PHOTOGRAPHIC ELEMENTS AND PROCESSES EMPLOYING SAME

[75] Inventors: Philip T. S. Lau, Rochester; Danny R. Thompson, Fairport, both of N.Y.

[73] Assignee: Eastman Kodak Company

[21] Appl. No.: 603,590

[22] Filed: Oct. 25, 1990

[51] Int. Cl.$^5$ .................. G03C 7/32; G03C 7/34; G03C 7/36; G03C 7/38
[52] U.S. Cl. .................. 430/385; 430/226; 430/543; 430/548; 430/533; 430/555; 430/55
[58] Field of Search .................. 430/558 R, 226, 543, 430/548, 553, 555, 557, 376, 385, 387, 389

[56] References Cited

U.S. PATENT DOCUMENTS

| | | | |
|---|---|---|---|
| 2,213,986 | 9/1940 | Kendall et al. | 430/548 |
| 2,476,008 | 7/1948 | Vittum et al. | 430/553 |
| 2,706,683 | 4/1955 | Sawdey | 430/548 |
| 3,227,550 | 1/1966 | Whitmore et al. | 430/543 |
| 3,419,390 | 12/1968 | Cressman et al. | 430/548 |
| 3,468,666 | 9/1969 | Shiba et al. | 430/548 |
| 4,028,106 | 6/1977 | Hori et al. | 96/55 |
| 4,477,560 | 10/1984 | Koitabashi et al. | 430/506 |
| 4,777,123 | 10/1988 | Yamada et al. | 430/505 |

Primary Examiner—Richard L. Schilling
Attorney, Agent, or Firm—Foley & Lardner

[57] ABSTRACT

A coupler having as a coupling-off group an alkyl group substituted with an electron source capable of stabilizing carbonium ion.

15 Claims, 2 Drawing Sheets

ALKYL SUBSTITUTED PHOTOGRAPHIC COUPLERS AND PHOTOGRAPHIC ELEMENTS AND PROCESSES EMPLOYING SAME

BACKGROUND OF THE INVENTION

This invention relates to novel photographic couplers and to silver halide photographic elements employing such couplers. In particular it relates to couplers containing novel coupling-off groups.

Images are commonly obtained in the photographic art by a coupling reaction between the development product of a silver halide developing agent (e.g., an oxidized aromatic primary amino developing agent) and a color-forming compound known as a coupler. The dyes produced by the coupling reaction are indoaniline, azomethine, indamine or indophenol dyes, depending on the chemical composition of the coupler and the developing agent. Ordinarily the subtractive process of color formation is employed, and the resulting image dyes are usually cyan, magenta and yellow dyes which are formed in or adjacent silver halide layers sensitive to red, green and blue radiation, respectively.

Color forming couplers employed in photographic materials commonly are either four-equivalent couplers or two-equivalent couplers (see G. Haist, Modern Photographic Processing, Vol. 2 (1979), pp. 478–495). Four-equivalent couplers require development of four molecules of silver halide in order ultimately to produce one molecule of dye. In the development process, two electrons per molecule of developing agent are transferred to silver halide, forming two silver atoms and a positively charged oxidized developing agent. The positively charged oxidized developing agent then reacts with the coupling agent. The coupling agent is negatively charged in alkaline solution due to loss of an active hydrogen, which leaves its binding pair of electrons behind (i.e., the active hydrogen leaves as $H^+$). Reaction of the negatively charged coupler with the positively charged oxidized developing agent forms a leuco dye. A subsequent oxidation of the leuco dye so formed, involving the transfer of two more electrons per molecule of developing agent to produce two more silver atoms, yields the dye.

Two-equivalent couplers require the development of only two molecules of silver halide to produce one molecule of dye. Two-equivalent couplers contain a substituent in the coupling position, known as a coupling-off group. The coupling-off group is eliminated as an anion, typically $ArO^-$, $ArS^-$, $RO^-$ or $RS^-$, upon reaction with the oxidized developing agent to form the leuco dye. The elimination of the anionic coupling-off group removes two bonding electrons with it, and thus essentially oxidizes the leuco dye to the desired dye without the need for transfer of electrons to two additional silver halide molecules.

Couplers substituted with alkyl groups at their coupling sites are known, such as the so-called "white couplers" (Agfa) used to scavenge oxidized developer in photographic elements However, such couplers do not form dyes, because the energy required to cleave the coupler-alkyl group carbon-carbon bond and thus form an anionic leaving group is very high. Moreover, the known alkyl group substituents cannot leave as cationic leaving groups, due to the great instability of the resultant carbonium ion. Thus, for all practical purposes the alkyl group can be considered as a non-leaving group. The known couplers substituted with alkyl groups thus react with the oxidation product of a color developing agent to form a stable leuco dye.

Cationic coupling-off groups are expected to have novel and useful properties, such as high reactivity with nucleophiles. A need therefore exists for a dye-producing photographic coupler having a cationic coupling-off group, in particular a coupler which employs an alkyl group as the coupling-off group.

SUMMARY OF THE INVENTION

The present invention solves this problem by means of a dye-forming coupler having the structure:

$$COUP-CHR-S_e$$

wherein
COUP is a dye-forming coupler moiety substituted in its coupling position with the remainder of the structure,
R is hydrogen, $(C_{1-6})$alkyl or unsubstituted or substituted $(C_{6-15})$aryl, and
$S_e$ is an electron source capable of stabilizing a carbonium ion.

It has been discovered that substitution of an alkyl group, in particular a methyl group, with an electron source capable of stabilizing a carbonium ion by resonance (i.e., charge delocalization) converts the alkyl group into an effective coupling-off group.

In another embodiment this invention relates to a photographic element comprising a support and a silver halide emulsion layer having associated therewith a dye-forming coupler as described above.

In yet another embodiment this invention relates to a process for developing an image in a photographic element by developing it in the presence of a dye-forming coupler as described above.

In still another embodiment this invention relates to a photographic silver halide emulsion comprising a dye-forming coupler as described above.

BRIEF DESCRIPTION OF THE DRAWINGS

The invention may be more readily understood by reference to the accompanying drawing in which.

DETAILED DESCRIPTION OF PREFERRED EMBODIMENTS

Substituents capable of acting as electron sources for use in the coupling-off groups according to the invention include substituents which comprise a heteroatom having an unshared pair of electrons, such as —OH and —NHR′, wherein R′ is an alkyl or aryl group. In the context of the present invention, it has been found to be especially advantageous to employ as the electron source an ionizable group capable of forming an anion at pH 10.0. Use of such an ionizable group results in formation of a negative charge, which stabilizes the positively-charged carbonium ion to an even greater extent than the electron pairs provided by electron sources such as amino groups. Couplers comprising coupling-off groups substituted with the foregoing ionizable groups are highly active.

In a particularly preferred embodiment, the ionizable group has the structural formula:

$$-L-NHSO_2-R_1$$

in which

L is a single bond, $-(-CR_3=CR_4-)_n-$,

[structure: $+CR_3=CR_4-\text{Ph}+_n$]

[structure: $+\text{Ph}-CR_3=CR_4+_n$]

[structures: phenyl with $R_3$ substituent, two variants]

[structures: naphthyl with $R_3$ substituent, two variants] or

[structure: 5-membered ring with $R_3$ and B]

n is 1 or 2,

B denotes atoms sufficient to complete a 5- or 6-member ring, wherein said atoms are selected from the group of C, N, O and S, $R_1$ is $(C_{1-20})$alkyl, unsubstituted or substituted $(C_{6-25})$aryl, a perfluoralkyl group with 1–5 carbon atoms, $-CO_2R_2$ or unsubstituted or substituted $(C_{6-25})$aryl-$CO_2R_2$, $R_2$ is H, $(C_{1-20})$alkyl or $(C_{6-25})$aryl, and $R_3$, $R_4$ are identical or different, and each is H, Cl, F, $-CN$, $-NO_2$, $-CF_3$, $-SCH_3$, $-SO_2CH_3$, $(C_{1-16})$alkyl, $(C_{1-16})$alkoxy, $-NHCO(C_{1-16})$alkyl, $-NHSO_2(C_{1-16})$alkyl or $-CO_2(C_{1-16})$alkyl.

The group L can in particular be a sequence of conjugated double bonds, or a sequence of alternating double bonds and aryl groups. Groups of this type permit a high degree of charge delocalization and thus lead to increased anion stabilization.

Examples of coupling-off groups according to the invention having especially preferred ionizable groups are shown below:

[structure: $-CH_2-\text{Ph}-NH-SO_2-\text{Ph}$]

[structure: $-CH_2-\text{Ph}-NH-SO_2-\text{Ph}-NO_2$]

[structure: $-CH_2-\text{o-tolyl}-NH-SO_2-\text{Ph}$]

[structure: $-CH_2-\text{o-tolyl}-NH-SO_2-C_4H_9\text{-n}$]

$-CH_2-NH-SO_2-R_3$,   $R_3 = C_{1-12}$ alkyl
$+CH=CH+_n NH-SO_2-CH_3$,   n = 1 to 3

[structure: pyrazole derivative with $-CH_2-$, $CH_3$, and $NH-SO_2-C_4H_9\text{-i}$]

Additional preferred coupling-off groups according to the invention include the following:

[structure: $-CH(\text{Ph})-NH-SO_2-CH_3$]

[structure: $-CH(\text{p-tolyl})-NH-SO_2-CH_3$]

[structure: $-CH(\text{p-NO}_2\text{-phenyl})-NH-SO_2-CH_3$]

[structure: $-CH(R_3)-NH-SO_2-\text{Ph}$]

Examples of representative couplers according to the invention are shown below:

| Coupler | Coupling-off group | Coupler | Coupling-off group |
|---|---|---|---|

(I)

A)  —CHR—S$_e$ = —CHR—OH

1)  —CH$_2$—OH

B)  —CHR—S$_e$ = —CH$_2$—NHR$_1$

2)

3)

C)  —CHR—S$_e$ = —CH$_2$—NH—SO$_2$—R$_1$

4)  —CH$_2$—NH—SO$_2$—C$_4$H$_9$-n

5)

6)  —CH$_2$—NH—SO$_2$—C$_{12}$H$_{25}$-n

E)  —CHR—S$_e$ = —CH$_2$—L—NH—SO$_2$—R$_1$

13)

14)

15) —CH$_2$—<benzene>—NH—SO$_2$—CH$_3$

16)

17) —CH$_2$—<benzene with NH—SO$_2$—C$_4$H$_9$-n>

18) —CH$_2$—<benzene with Cl and NH—SO$_2$—CO$_2$H>

19)

20)

-continued

| Coupler | Coupling-off group | Coupler | Coupling-off group |
|---|---|---|---|
| 7) | $-CH_2-NH-SO_2-C_6H_5$ (phenyl) | 21) | $-CH_2-$ (naphthyl with $NH-SO_2-CH_3$) |
| 8) | $-CH_2-NH-SO_2-CO_2-C_2H_5$ | 22) | $-CH_2-CH=CH-NH-SO_2-CH_3$ |
| 9) | $-CH_2-NH-SO_2-CO_2H$ | 23) | $-CH_2-(-CH=CH-)_2-NH-SO_2-CH_3$ |
| 10) | $-CH_2-NH-SO_2-CF_3$ | 24) | $-CH_2-C_6H_4-CH=CH-NH-SO_2-C_6H_5$ |
| D) | $-CHR-S_e = -CH_2-L-OH$ | 25) | $-CH_2-CH=CH-C_6H_4-NH-SO_2-C_6H_5$ |
| 11) | $-CH_2-CH=CH-OH$ | F) | $-CHR-S_e = -CHR-NH-SO_2-R_1$ |
| 12) | $-CH_2-$ (phenyl with $CO_2-C_2H_5$ and $OH$) | 26) | $-CH(CH_3)-NH-SO_2-C_6H_5$ |
| | | 27) | $-CH(C_6H_5)-NH-SO_2-CH_3$ |
| | | 28) | $-CH_2(C_6H_5)-NH-SO_2-C_6H_5$ |

(II)

Structure: naphthalene with $OH$, $C(=O)-NH(CH_2)_3-O-C_{12}H_{25}\text{-}n$, $(CH_3)_2CHCH_2-O-C(=O)-NH$, and $CHR-S_e$ substituents.

| Coupler | Coupling-off group | Coupler | Coupling-off group |
|---|---|---|---|
| A) | $-CHR-S_e = -CH_2-NH-SO_2-R_1$ | B) | $-CHR-S_e = -CH_2-L-NH-SO_2-R_1$ |
| 29) | $-CH_2-NH-SO_2-C_6H_5$ | 33) | $-CH_2-C_6H_4-NH-SO_2-C_6H_4-CN$ |
| 30) | $-CH_2-NH-SO_2-C_2H_5$ | C) | $-CHR-S_e = -CH_2-L-OH$ |
| 31) | $-CH_2-NH-SO_2-C_4H_9$ | 34) | $-CH_2-C_6H_4-CH=CH-OH$ |
| 32) | $-CH_2-NH-SO_2-CF_3$ | | |

-continued

| Coupler | Coupling-off group | Coupler | Coupling-off group |
|---|---|---|---|

(III)

[Structure III: 1-(2,4,6-trichlorophenyl)-pyrazolone coupler with -NH-C(=O)-C6H4-NH-C(=O)-CH2-O-C6H3(C5H11-t)2 substituent and CHR-Se group]

| A) | $-CHR-S_e = -CHR-NH-SO_2-R_1$ | B) | $-CHR-S_e = -CHR-L-NH-SO_2-R_1$ |
|---|---|---|---|

35) $-CH_2-NH-SO_2-C_4H_9\text{-n}$

45) $-CH_2-\text{C}_6\text{H}_4-NH-SO_2-\text{C}_6\text{H}_5$

36) $-CH_2-NH-SO_2-C_{12}H_{25}\text{-n}$

46) $-CH_2-(2,5\text{-dichlorophenyl})-NH-SO_2-CH_3$

37) $-CH_2-NH-SO_2-\text{C}_6\text{H}_5$

47) $-CH_2-\text{C}_6\text{H}_4-NH-SO_2-C_4H_9\text{-n}$

38) $-CH(CH_3)-NH-SO_2-\text{C}_6\text{H}_5$

48) $-CH_2-(3\text{-CN-phenyl})-NH-SO_2-\text{C}_6\text{H}_5$

39) $-CH(C_{12}H_{25}\text{-n})-NH-SO_2-\text{C}_6\text{H}_5$

49) $-CH_2-(3\text{-CN-phenyl})-NH-SO_2-CH_3$

40) $-CH(C_4H_9\text{-n})-NH-SO_2-\text{C}_6\text{H}_4-NO_2$

50) $-CH_2-$ [3-methyl-1-phenyl-5-(NH-SO$_2$-C$_4$H$_9$-i)-pyrazol-4-yl]

41) $-CH(\text{C}_6\text{H}_5)-NH-SO_2-CH_3$

42) $-CH(4\text{-CH}_3\text{-C}_6\text{H}_4)-NH-SO_2-CH_3$

-continued

| Coupler | Coupling-off group | Coupler | Coupling-off group |
|---|---|---|---|

43) −CH(−C₆H₄-4-NO₂)−NH−SO₂−CH₃

44) −CH(−C₆H₄-4-NO₂)−NH−SO₂−C₆H₄−CH₃

(IV) 1-(2,4,6-trichlorophenyl)-3-{[2-chloro-5-(2-(3-t-butyl-4-hydroxyphenoxy)tetradecanamido)anilino]}-4-(CHR−S_e)-pyrazol-5-one A) −CHR−S_e = −CHR−NH−SO₂−R₁  
B) −CHR−S_e = −CHR−L−NH−SO₂−R₁

51) −CH(CH₃)−NH−SO₂−C₆H₄-4-NO₂

54) −CH₂−C₆H₄−NH−SO₂−C₆H₅

52) −CH(−C₆H₄-4-OCH₃)−NH−SO₂−CH₃

53) −CH(−C₆H₄-4-NO₂)−NH−SO₂−C₆H₄−CH₃

(V) pyrazolo-triazole coupler with −(CH₂)₃−C₆H₄−NHCO−CH(C₁₀H₂₁-n)−O−C₆H₄−SO₂−C₆H₄−OH substituent and CHR−S_e group A) −CHR−S_e = −CHR−NH−SO₂−R₁  
B) −CHR−S_e = −CHR−L−NH−SO₂−R₁

55) −CH(CH₃)−NH−SO₂−C₆H₄-4-NO₂

58) −CH₂−C₆H₄−NH−SO₂−C₆H₅

| Coupler | Coupling-off group | Coupler | Coupling-off group |
|---|---|---|---|

56) $-\text{CH}-\text{NH}-\text{SO}_2-\text{CH}_3$ attached to phenyl with $-\text{O}-\text{CH}_3$ 57) $-\text{CH}-\text{NH}-\text{SO}_2-$ (phenyl-$\text{CH}_3$), with phenyl bearing $-\text{NO}_2$ (VI)

Structure: n-$\text{C}_4\text{H}_9-\text{CH}-\overset{O}{\overset{\|}{\text{C}}}-\text{NH}-$[phenyl with OH, CHR—$S_e$]$-\text{NH}-\overset{O}{\overset{\|}{\text{C}}}-\text{NH}-$phenyl$-\text{CN}$, with O-phenyl($\text{C}_5\text{H}_{11}$-t)($\text{C}_5\text{H}_{11}$-t)

59) $-\text{CH}_2-\text{NH}-\text{SO}_2-$phenyl$-\text{CO}_2-\text{C}_2\text{H}_5$ 60) $-\text{CH}_2-\text{NH}-\text{SO}_2-\text{CH}_3$ (VII)

Structure: phenyl with OH, Cl, $\text{C}_2\text{H}_5$, CHR—$S_e$, $-\text{NH}-\overset{O}{\overset{\|}{\text{C}}}-\text{CH}(\text{C}_2\text{H}_5)-\text{O}-$phenyl($\text{C}_5\text{H}_{11}$-t)($\text{C}_5\text{H}_{11}$-t)

61) $-\text{CH}_2-\text{NH}-\text{SO}_2-\text{C}_4\text{H}_9$-n

62) $-\text{CH}_3-\text{NH}-\text{SO}_2-$phenyl$-\text{CO}_2\text{H}$ (VIII)

Structure: naphthalene with OH, CHR—$S_e$, $-\overset{O}{\overset{\|}{\text{C}}}-\text{NH}-$phenyl$-\text{O}-\text{CH}(\text{CH}_3)(\text{C}_{12}\text{H}_{25}$-n$)$ 63) $-\text{CH}_2-\text{NH}-\text{SO}_2-\text{CH}_3$ As used herein, the terms "coupler" and "coupler compound" refer to the entire compound, including the coupler moiety COUP and the entire coupling-off group. The term "coupler moiety" refers to that portion of the compound other than the coupling-off group.

The coupler moiety COUP can be any moiety that will react with oxidized color developing agent to cleave the bond between the alkyl portion of the coupling-off group and the coupler moiety. The coupler moiety typically is a known coupler which has no coupling-off group at its coupling position Said moiety can be ballasted or unballasted.

The couplers according to the invention can be used in the ways and for the purposes that couplers are used in the photographic art. Those couplers which are ballasted, and hence immobile in the layers of photographic elements, can be associated with a silver halide emulsion layer, while those couplers which are diffusible can be incorporated in silver halide developer compositions and brought into contact with the silver halide emulsion during processing.

A large number of couplers which provide magenta and cyan dye images, as well as yellow and black dye images, are known. These known couplers can be substituted at their coupling positions with the novel coupling-off groups to yield couplers according to the invention. Preferred couplers which form cyan dyes upon reaction with oxidized color developing agents are phenols and naphthols. Representative couplers are described in the following patents and publications: U.S. Pat. Nos. 2,367,531; 2,423,730; 2,474,293; 2,772,162; 2,895,826; 3,002,836; 3,034,892; 3,041,236; 4,333,999; and in "Farbkuppler—ein Literaturübersicht," published in Agfa Mitteilungen, Band III, pp. 156-175 (1961).

Structures of preferred cyan couplers include the following:

where $R_6$ and $R_7$ are chosen independently to be a ballast group, unsubstituted or substituted alkyl, or phenyl or substituted phenyl, and the coupling-off group —CHR—A is as defined above.

Preferred couplers which form magenta dyes upon reaction with oxidized color developing agents are pyrazolones, pyrazolotriazoles, pyrazolobenzimidazoles and indazolones. Typical couplers are described in U.S. Pat. Nos. 2,311,082; 2,343,703; 2,369,489; 2,600,788; 2,673,801; 2,908,573; 3,061,432; 3,062,653; 3,152,896; 3,519,429; and 3,725,067 and in "Farbkuppler—ein Literaturübersicht," published in Agfa Mitteilungen, Band III, pp. 126-156 (1961).

Structures of preferred magenta couplers include the following:

where $R_6$ and $R_7$ are chosen independently to be a ballast group, unsubstituted or substituted alkyl, or phenyl or substituted phenyl, and the coupling-off group —CHR—$S_e$ is as defined above.

Couplers which form yellow dyes upon reaction with oxidized color developing agents are typically acylacetanilides such as benzoylacetanilides and pivalylacetanilides. Representative couplers are described in U.S. Pat. Nos. 2,298,443; 2,407,210; 2,875,057; 3,048,194; 3,265,506; and 3,447,928, and in "Farbkuppler—ein Literaturübersicht," published in Agfa Mitteilungen, Band III, pp. 112-126 (1961).

Couplers which form black dyes upon reaction with oxidized color developing agents are preferably resorcinols or m-aminophenols. Typical couplers are described in U.S. Pat. Nos. 1,939,231; 2,181,944; 2,333,106; and 4,126,461; German OLS No. 2,644,194 and 2,650,764.

Most preferably, the coupler moieties COUP in the couplers according to the invention are cyan or magenta coupler moieties.

The photographic couplers according to the invention can be incorporated in photographic elements. They can also be incorporated in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, the couplers generally are non-diffusible, i.e., they are of such molecular size and configuration that they will not diffuse or wander from the layer in which they are coated to any significant extent.

Photographic elements according to the invention can be processed by conventional techniques in which color forming couplers and color developing agents are incorporated in separate processing solutions or compositions or in the element itself.

Photographic elements in which the couplers according to the invention are incorporated can be simple elements comprising a support and a single silver halide emulsion layer, or they can be multilayer, multicolor elements. The couplers according to the invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated therewith other photographic coupler compounds, such as colored masking couplers or competing couplers These other photographic couplers can form dyes of the same or different color and hue as the couplers according to the invention. In addition, the silver halide emulsion layers and other layers of the photographic element can contain other conventional additives.

A typical multilayer, multicolor photographic element can comprise a support having thereon a red-sensitive silver halide .emulsion unit having associated therewith a cyan dye image-forming material, a green-sensitive silver halide emulsion unit having associated therewith a magenta dye image-forming material, and a blue-sensitive silver halide emulsion unit having associated therewith a yellow dye image-forming material, wherein at least one of the foregoing silver halide emulsion units, preferably at least one of the red- and blue-sensitive silver halide emulsion units, has associated therewith a coupler according to the invention. Each silver halide emulsion layer can comprise one or more layers. The various units and layers moreover can be arranged in different locations with respect to one another.

The photographic elements can be single color elements or multicolor elements Multicolor elements contain dye image-forming units sensitive to each of the three primary regions of the spectrum. Each unit can comprise a single emulsion layer or multiple emulsion layers sensitive to a given region of the spectrum The layers of the element, including the layers of the image-forming units, can be arranged in various orders known to those skilled in the art. In an alternative format, the emulsions sensitive to each of the three primary regions of the spectrum can be disposed as a single segmented layer, e g., as by the use of microvessels as described in Whitmore, U.S. Ser. No. 184,714, filed Sept. 8, 1980.

A typical multicolor photographic element can also contain additional layers, such as filter layers, interlayers, overcoat layers, subbing layers and the like.

The light-sensitive silver halide emulsions can include coarse, regular or fine grain silver halide crystals or mixtures thereof and can comprise such silver halides as silver chloride, silver bromide, silver bromoiodide, silver chlorobromoiodide and mixtures thereof The emulsions can be negative-working or direct-positive. They can form latent images predominantly on the surface of the silver halide grains or predominantly on the interior of the silver halide grains. They can be chemically and spectrally sensitized. The emulsions typically will be gelatin emulsions although other hydrophilic colloids are also useful.

Preferably, the couplers according to the invention are incorporated in silver halide emulsions and the emulsions coated on a support to form a photographic element Alternatively, the inventive couplers can be incorporated in photographic elements adjacent the silver halide emulsion where, during development, the coupler will be in reactive association with development products such as oxidized color developing agent. Thus, as used herein, the term "associated therewith" signifies that the coupler is in a silver halide emulsion layer or in an adjacent location where, during processing, it will come into reactive association with silver halide development products.

The support can be any support used with photographic elements. Typical supports include cellulose nitrate film, cellulose acetate film, polyvinylacetal film, polyethylene terephthalate film, polycarbonate film and related films or resinous materials, as well as glass, paper, metal and the like. Typically, a flexible support is employed, such as a polymeric film or paper support. Paper supports can be acetylated or coated with baryta and/or and α-olefin polymer, particularly a polymer of an α-olefin containing 2 to 10 carbon atoms such as polyethylene, polypropylene, ethylenebutene copolymers and the like.

In the following discussion of suitable materials for use in the emulsions and elements according to the invention, reference will be made to *Research Disclosure*, December 1989, Item 308119, published by Kenneth Mason Publications Ltd , Elmsworth, Hampshire P010 7DQ, U.K., the disclosures of which are incorporated in their entireties herein by reference. This publication will be identified hereafter as "Research Disclosure".

The silver halide emulsions employed in the elements according to the invention can be either negative-working or positive-working. Suitable emulsions and their preparation are described in Research Disclosure Sections I and II and the publications cited therein Suitable vehicles for the emulsion layers and other layers of elements according to the invention are described in Research Disclosure Section IX and the publications cited therein.

In addition to the couplers according to the invention, the elements according to the invention can include additional couplers as described in Research Disclosure Section VII, paragraphs D, E, F and G and the publications cited therein These couplers can be incorporated in the elements and emulsions as described in Research Disclosure Section VII, paragraph C and the publications cited therein.

The photographic elements according to the invention, or individual layers thereof, can contain brighteners (see Research Disclosure Section V), antifoggants and stabilizers (see Research Disclosure Section VI), antistain agents and image dye stabilizers (see Research Disclosure Section VII, paragraphs I and J), light-absorbing and scattering materials (see Research Disclosure Section VIII), hardeners (see Research Disclosure Section X), plasticizers and lubricants (see Research Disclosure Section XII), antistatic agents (see Research Disclosure Section XIII), matting agents (see Research Disclosure Section XVI), and development modifiers (see Research Disclosure Section XXI).

The photographic elements according to the invention can be coated on a variety of supports as described in Research Disclosure Section XVII and the references cited therein.

Photographic elements can be exposed to actinic radiation, typically in the visible region of the spectrum, to form a latent image as described in Research Disclosure Section XVIII, and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N,N-diethylaniline hydrochloride, 4-amino-3-methyl-N-ethyl-N-β-(methanesulfonamido)ethylaniline sulfate hydrate, 4-amino-3-β-(methanesulfonamido) ethyl-N,N-diethylaniline hydrochloride and 4-amino-N-ethyl-N-(2-methoxyethyl)-m-toluidine di-p-toluene sulfonic acid.

With negative-working silver halide this processing step leads to a negative image. To obtain a positive (or reversal) image, this step can be preceded by development with a non-chromogenic developing agent to develop exposed silver halide, but not form dye, then uniformly fogging the element to render unexposed silver halide developable, followed by development with a chromogenic developer. Alternatively, a direct-positive emulsion can be employed to obtain a positive image.

Development is followed by the conventional steps of bleaching, fixing, or bleach-fixing, to remove silver and silver halide, washing and drying.

Couplers according to the invention can be prepared by reactions and methods known to those skilled in the organic synthesis art. Exemplary procedures are shown in Schemes A–C, below. Syntheses of particular couplers according to the invention are presented in the following examples.

perature for 3 hours The reaction mixture was filtered through super-cel to remove the catalyst. The filtrate was distilled under reduced pressure to give a residual solid. Recrystallization from $CH_3CN$ gave 13.8 g (91%) of lustrous white crystalline plates (compound III), m.p. 156°-157° C.

Calculated for $C_{32}H_{43}NO_4$: C, 76.0; H, 8.57; N, 2.77. Found: C, 75.94; H, 8.71; N, 2.67.

SYNTHESIS EXAMPLE 2

Preparation of Coupler No. 2

A mixture of 15.1 g (0.03 mole) of compound II and 2.9 g (0.03 mole) aniline in 200 ml toluene was refluxed for 5 hours, and the water was azeotropically distilled off into a Dean Stark trap After the reaction was completed the toluene solvent was removed under reduced pressure to give the essentially pure Schiff base compound IV ($R_1$=phenyl) as a yellow oil. The oil, was taken up in 150 ml EtOAc and reduced for 4 hours under 40 lbs of $H_2$ with 10% Pd/C catalyst The reduced mixture was filtered through super-cel, and the filtrate was distilled under reduced pressure to give an oil The oil was dissolved in hot $CH_3CN$ and allowed to crystallize out at room temperature. The white crystalline solid was collected and dried to give 10.6 g (61%) of the desired product, compound V ($R_1$=phenyl), m p. 139°-140° C.

Calculated for $C_{32}H_{48}N_2O_3$: C, 78.58; H, 8.33; N 4.82. Found: C, 78.54; H, 8.31; N, 4.90.

SYNTHESIS EXAMPLE 3

Preparation of Coupler No. 6

Step 1:

A mixture of 47.6 g (0.10 mol) of compound I, 14.0 g (0.10 mol) hexamethylenetetramine and 12.6 g (0.10 mol) sodium sulfite in 250 ml glacial acetic acid was stirred at room temperature for 30 minutes, then heated on a steam bath for 4 hours. Upon cooling to room temperature, a bright yellow solid (compound II) crystallized out. The solid was collected, washed with methanol and dried. Thin layer chromatography (EtOAC—$CH_2Cl_2$ 1:1) showed the product to be pure. Yield was 46.6 g (93%), m.p. 170°-171° C. The structure was consistent with the $^1H$ NMR spectrum of compound II.

Calculated for $C_{32}H_{41}NO_4$: C, 76.31; H, 8.21; N, 2.78. Found: C, 76.12; H, 8.15; N, 2.70.

Step 2:

To a solution of 30.2 g (0.06 mol) of compound II in 200 ml DMSO was added with stirring 8.3 g (0.12 mol) hydroxylamine hydrochloride dissolved in 25 ml water. The mixture was heated with stirring on a steam bath for 2 hours Upon cooling to room temperature the mixture was poured into ice-water. The precipitated solid (compound VI) was collected, washed thoroughly with water and air dried The crude solid was recrystallized from ethanol-heptane to give 22.7 g (73%) of crystalline plates, m.p. 130°-132° C. The structure was consistent with the $^1H$ NMR spectrum of compound VI.

Calculated for $C_{32}H_{42}N_2O_4$: C, 74.10; H, 8.16; N, 5.40. Found: C, 73.95; H, 8.18; N, 5.30.

Step 3:

To a solution of 5.2 g (0.01 mol) of compound VI in 100 ml of ethanol was added 1.5 ml concentrated HCl and a spoonful of 5% palladium-on-charcoal catalyst. The mixture was reduced under 45 lbs of hydrogen at

SYNTHESIS EXAMPLE 1

Preparation of Coupler No. 1

Step 1:

A mixture of 23.8 g (0.05 mole) of compound I (shown in Scheme A), 7.1 g (0.05 mole) of hexamethylenetetramine and 6.3 g (0.05 mole) of sodium sulfite in 150 ml glacial acetic acid was heated with stirring on a steam bath for 4 hours. Upon cooling to room temperature long needles crystallized out. The solid was collected, washed with a small amount of methanol and air dried to give 23.3 g (93%) of pure compound (II), melting point (m.p.) 170°-171° C.

Calculated for $C_{32}H_{41}NO_4$: C, 76.31; H, 8.21; N, 2.78. Found: C, 76.12; H, 8.15; N,2.70.

Step 2:

A solution of 15.1 g (0.03 mole) of compound II in 150 ml tetrahydrofuran and a spoonful of Raney nickel catalyst was reduced under 45 lbs of Hz at room temroom temperature. After the reduction the mixture was filtered to remove the catalyst. The ethanol solvent was removed under reduced pressure. The resulting residue was triturated with ether to give a white solid (compound VII). The solid was collected and dried. Yield was 4.5 g (83%), m.p. 98°-100° C. Thin layer chromatography (EtOAC—heptane 1:1) showed one product spot. The structure was consistent with the $^1$H NMR spectrum of compound VII.

Calculated for $C_{32}H_{45}ClN_2O_3$: C, 71.02; H, 8.38; N, 5.18. Found: C, 69.94; H, 8.15; N, 5.08.

Step 4:

To a mixture of 16.2 g (0.03 mol) of compound VII in 200 ml of tetrahydrofuran was added with stirring 15.2 g (0.15 mol) triethylamine. A white precipitate of triethylamine hydrochloride was formed immediately. A solution of 8.1 g (0.03 mol) of dodecanesulfonyl chloride in 50 ml tetrahydrofuran was added slowly to the free amine solution. The mixture was stirred at room temperature for 3 hours and then poured into ice water containing 10 ml of concentrated HCl. The solid which separated was collected, washed with water and dried. The crude product was recrystallized from ethanol to give 17.3 g (78.2%) of a white solid (compound VIII, $R_1=C_{12}H_{25}$—n), m.p. 144°-145° C. The structure was consistent with the $^1$H NMR spectrum of the desired product.

Calculated for $C_{44}H_{68}N_2O_5S$: C, 71.70; H, 9.30; N, 3.80. Found: C, 71.65; H, 9.17; N, 3.81.

SYNTHESIS EXAMPLE 4

Preparation of Coupler No. 5

Step 1:

To a solution of 63 g (0.12 mole) of compound II in 350 ml DMSO was added slowly with stirring 17.4 g (0.25 mole) hydroxylamine hydrochloride dissolved in 50 ml water. The mixture was heated with stirring on a steam bath for 2 hours. After cooling to room temperature the mixture was drowned in water. The solid was collected, washed with water and dried. Recrystallization from EtOH-heptane yielded 47.2 g (73%) of compound VI, m.p. 130°-132° C.

Calculated for $C_{32}H_{42}N_2O_4$: C, 74.10; H, 8.16; N, 5.40. Found: C, 74.45; H, 8.18, N, 5.30.

Step 2:

To a solution of 10.4g (0.02 mole) of the oxime compound VI prepared above in 100 ml EtOH was added 2.5 ml concentrated HCl and a spoonful of 5% Pd/C catalyst. The mixture was reduced under 45 lbs. of hydrogen at room temperature for 5 hours. The catalyst was removed by filtering through a super-cel pad. The ETOH solvent was removed under reduced pressure to give an oil which solidified upon trituration with ether. The solid was collected to give 9.0 g (83%) of the desired amine hychochloride salt (compound VII), m.p 98°-100° C. The amine was used as such without further purification for the synthesis of couplers 4, 5 and 10 (Table I) using the general procedure described below:

To a solution of 0.02 mole of the amine hydrochloride (compound VII) in 150 ml pyridine was added slowly with stirring 0 02 mole of the appropriate sulfonyl chloride. The reaction temperature was maintained below 35° C. After stirring at room temperature for 4 hours, the mixture was poured into ice water. The precipitated solid was collected, washed thoroughly with water and dried. The product was purified by recrystallization from an appropriate solvent or mixture of solvents. The m.p. and elemental analytical data of representative examples are given below:

TABLE I

| Coupler | m.p. (°C.) | | Elemental analysis | | |
|---|---|---|---|---|---|
| | | | C | H | N |
| 4 | 179-180° | | $C_{36}H_{52}N_2O_5S$: | | |
| | | c: | 69.20 | 8.39 | 4.48 |
| | | f: | 69.10 | 8.09 | 4.34 |
| 5 | 201-202° | | $C_{38}H_{48}N_2O_5S$: | | |
| | | c: | 70.78 | 7.50 | 4.34 |
| | | f: | 70.33 | 7.30 | 4.28 |
| 10 | 160-161° | | $C_{33}H_{43}F_3N_2O_5S$: | | |
| | | c: | 62.25 | 6.81 | 4.40 |
| | | f: | 62.15 | 6.77 | 4.37 |

SYNTHESIS EXAMPLE 5

Preparation of Coupler No. 13

Step 1:

A solution mixture of 9.52 g (0.02 mole) of compound I (shown in Scheme B), 6.2 g (0.022 mole) of 4-phenyl-sulfonamidochlorotoluene (compound IX, $R_1$=phenyl) and 4 6 g (0.04 mole) of tetramethylguanidine (TMG) in 200 ml THF was refluxed with stirring for 3 hours. After cooling to room temperature the mixture was drowned in ice-water containing 2 ml concentrated HCl. The solid was collected and recrystallized from EtOH to give 11.0 g (75%) of the desired coupler, compound X ($R_1$=phenyl), m.p. 178°-179° C.

Calculated for $C_{44}H_{52}N_2O_5S$: C, 73.30; H, 7.27; N, 3.89. Found: C, 73.33; H, 7.21; N, 3.84.

Similarly, other couplers according to the invention containing the same coupling-off group (COG) or variations thereof having other $R_1$ groups can be prepared using the above procedure.

SYNTHESIS EXAMPLE 6

Preparation of Coupler No. 44

Step 1:

To a solution of 6.7 g (0.01 mole) of compound XI (shown in Scheme C) and 3.0 g (0.01 mole) of compound XII (R=nitrophenyl, $R_1$=tolyl) in 150 ml THF was added dropwise with stirring 1.0 g (0.01 mole) of $Et_3N$. The reaction temperature was kept below 30° C. during the addition. After stirring at room temperature for 30 minutes, the mixture was poured into ice water containing 2 ml of concentrated HCl. The gummy solid was separated and washed with water. It was taken up in 30 ml EtOH. Upon standing at room temperature for 15 minutes a mass of white solid crystallized out. The solid was collected and dried to give 9.2 g (94%) of the desired coupler compound XIII, m.p. 155°-157° C. (dec.)

Calcd. for $C_{48}H_{49}Cl_1N_6O_8S$: C, 59.05; H, 5.06; N, 8.61. Found: C, 59.09; H, 5.05; N, 8.63.

Similarly, other couplers according to the invention which contain the foregoing coupling-off group or variations thereof can be prepared using the procedure described above.

USE EXAMPLE

Preparation of photographic element

Single-layer photographic elements were prepared by coating a cellulose acetate-butyrate film support with a photosensitive layer containing a silver bromide emulsion at 84.2 mg/ft$^2$, gelatin at 350 mg/ft$^2$ and an image coupler (0.15 mmol/ft$^2$) as shown in Table II dispersed in half its weight of dibutyl phthalate. The photosensitive layer was overcoated with a layer containing gelatin at 250 mg/ft² and bis-vinylsulfonyl methyl ether hardener at 1.75 wt % based on the total gel weight.

Samples of each element were exposed imagewise through a stepped density test object and processed at 100° F. employing the following color developing solution, then stopped with a low pH bath, bleached, fixed, washed and dried to produce stepped colored images.

| Color developer solution (3'15") | |
|---|---|
| K₂CO₃ | 37.50 g |
| Na₂SO₃ | 4.25 g |
| KI | 0.02 g |
| NaBr | 1.30 g |
| Hydroxylamine sulfate | 2.00 g |
| 4-Amino-3-methyl-N-ethyl N-B'-hydroxyethylaniline sulfate | 3.55 g |
| Water to make 1 liter, pH 10.0 | |
| Low pH bath: 3% acetic acid (2') | |
| Bleach (4') | |
| Ammonium bromide | 150.00 g |
| Ammonium ferric EDTA (1.56M) | 175.00 ml |
| Acetic acid | 9.50 ml |
| Sodium Nitrate | 35.00 g |
| Water to make 1 liter, pH 6.0 | |
| Wash (1') | |
| Fix (4') | |
| Ammonium thiosulfate | 214.00 g |
| (Ethylenedinitrilo)tetraacetic acid, di-Na+ salt | 1.29 g |
| Sodium metabisulfite | 11.00 g |
| NaOH (50%) | 4.70 g |
| Water to make 1 liter, pH 6.5 | |
| Wash (4') | |

Figure 1:
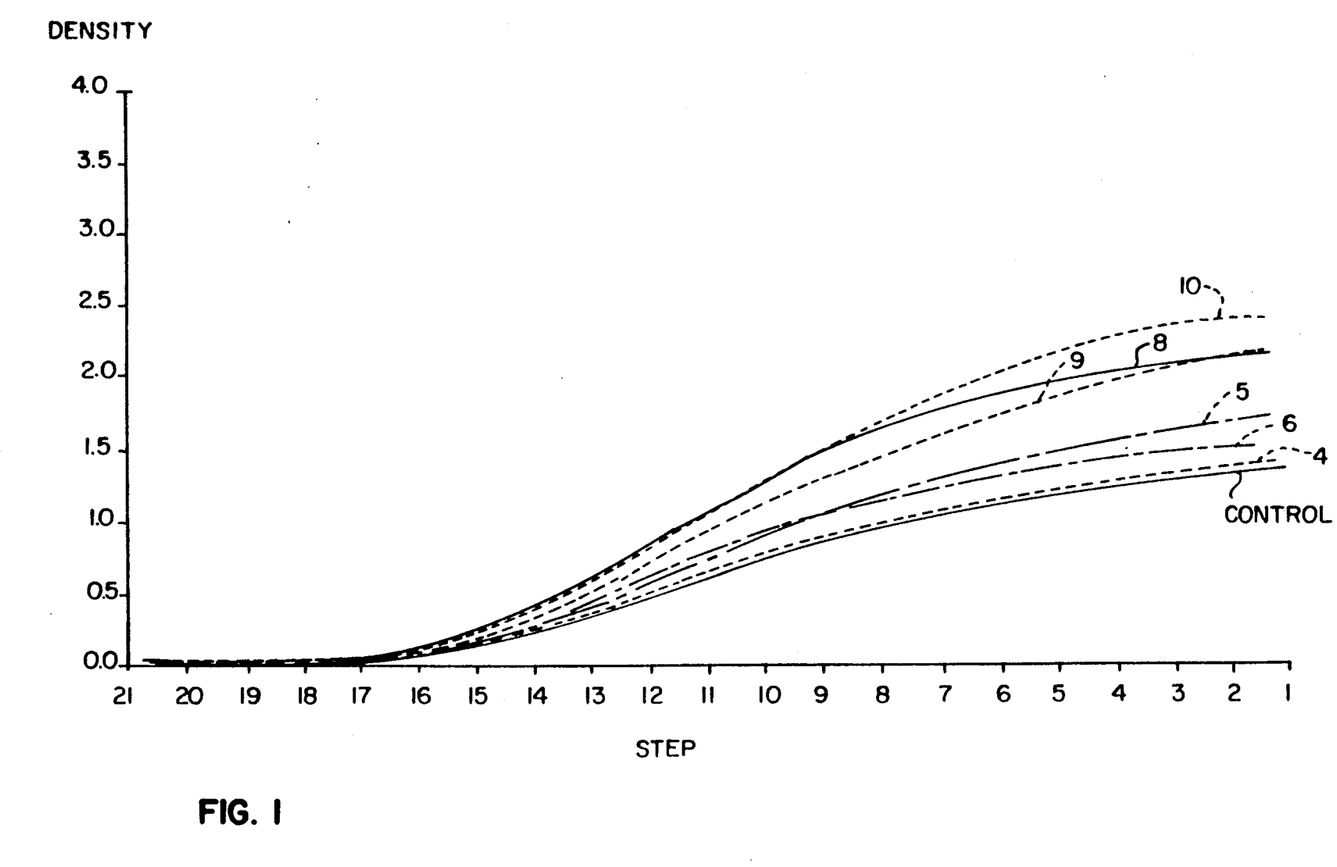
FIG. 1 is a graph showing maximum dye density v. exposure step for couplers according to the invention.
Figure 2:
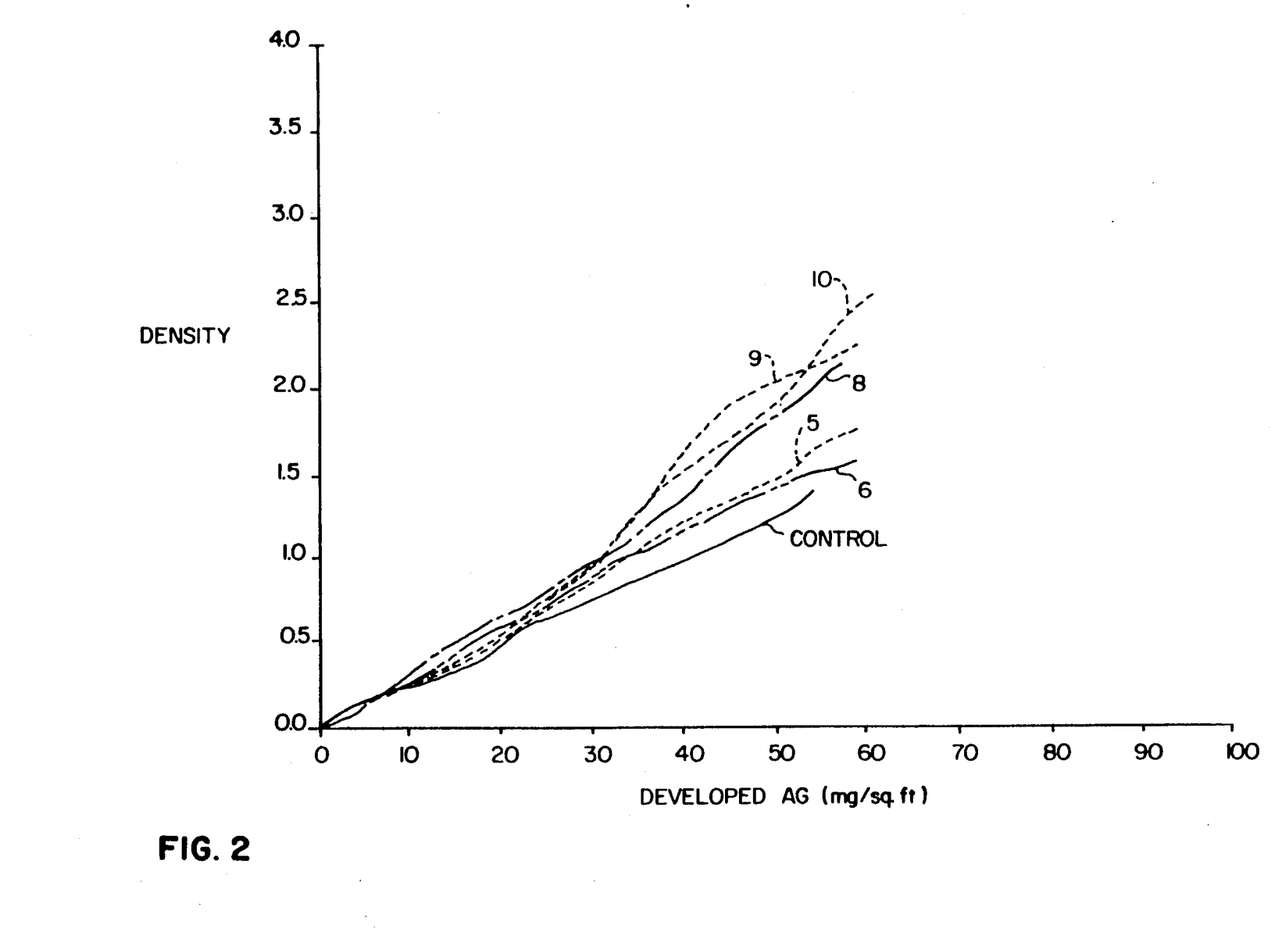
FIG. 2 is a graph showing activity maximum dye density v. developed Ag for couplers according to the invention.

Densitometry in the appropriate color region of these images provided the measure of the minimum and maximum density ($D_{min}$ and $D_{max}$) and gamma, defined as the maximum slope between any two adjacent density points. The results are shown in Table II and in FIGS. 1-2. Couplers according to the invention clearly provide superior $D_{max}$ as compared to the control coupler without a coupling -off group.

TABLE II

| Coup | Coupling-off group | $D_{max}$ | $D_{min}$ | γ |
|---|---|---|---|---|
| * | —H | 1.41 | 0.05 | 0.43 |
| 4 | —CH₂—NH—SO₂—C₄H₉-n | 1.51 | 0.05 | 0.50 |
| 5 | —CH₂—NH—SO₂—⟨phenyl⟩ | 1.78 | 0.04 | 0.67 |
| 6 | —CH₂—NH—SO₂—C₁₂H₂₅-n | 1.58 | 0.05 | 0.60 |
| 8 | —CH₂—NH—SO₂—CO₂—C₂H₅ | 2.22 | 0.05 | 0.77 |
| 9 | —CH₂—NH—SO₂—CO₂H | 2.20 | 0.06 | 0.87 |
| 10 | —CH₂—NH—SO₂—CF₃ | 2.58 | 0.05 | 0.87 |
| 0 | —CH₃ | 0.20 | 0.04 | 0.00 |

*control coupler
Coupler 0 formed no dye, as expected.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

Having thus described the invention, what is claimed as new and desired to be secured by Letters Patent is:

1. A photographic element comprising a support and a silver halide emulsion layer having associated therewith a dye-forming coupler having the structure:

$$\text{COUP—CHR—S}_e$$

wherein
COUP is a dye-forming coupler moiety substituted in its coupling position with the remainder of the structure,
R is hydrogen, (C₁₋₆)alkyl or unsubstituted or substituted (C₆₋₁₅)aryl, and
$S_e$ is represented by the formula

$$\text{—L—NHSO}_2\text{—R}_1$$

in which
L is a single bond, —(—CR₃═CR₄—)ₙ—, n is 1 or 2,
B denotes atoms sufficient to complete a 5- or 6-member ring, wherein said atoms are selected from the group of C, N, O and S,
R₁ is (C₁₋₂₀)alkyl, unsubstituted or substituted (C₆₋₂₅)aryl, or —CO₂R₂,
R₂ is H, (C₁₋₂₀)alkyl or (C₆₋₂₅)aryl, and
R₃, R₄ are identical or different, and each is H, Cl, F, —CN, —NO₂, —CF₃, —SCH₃, —SO₂CH₃, (C₁₋₁₆)alkyl, (C₁₋₁₆)alkoxy, —NHCO(C₁₋₁₆)alkyl, —NHSO₂(C₁₋₁₆)alkyl or —CO₂(C₁₋₁₆)alkyl.

2. A photographic element as claimed in claim 1, wherein $S_e$ is —NHSO₂R₁.

3. A photographic element as claimed in claim 1, wherein COUP is a magenta or cyan dye-forming coupler moiety.

4. A multicolor photographic element comprising a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, at least one of said cyan and magenta dye-forming couplers being a coupler having the structure:

COUP-13 CHR—S$_e$ wherein
COUP is a dye-forming coupler moiety substituted in its coupling position with the remainder of the structure,
R is hydrogen, (C$_{1-6}$)alkyl or unsubstituted or substituted (C$_{6-15}$)aryl, and
S$_e$ is represented by the formula

—L—NHSO$_2$—R$_1$ in which
L is a single bond, —(—CH$_3$=CR$_4$—)$_n$—, n is 1 or 2,
B denotes atoms sufficient to complete a 5- or 6-member ring, wherein said atoms are selected from the group of C, N, O and S,

R$_1$ is (C$_{1-20}$)alkyl, unsubstituted or substituted (C$_{6-25}$)aryl, or —CO$_2$R$_2$,
R$_2$ is H, (C$_{1-20}$)alkyl or (C$_{6-25}$)aryl, and
R$_3$, R$_4$ are identical or different, and each is H, Cl, F, —CN, —NO$_2$, —CF$_3$, —SCH$_3$, —SO$_2$CH$_3$, (C$_{1-16}$)alkyl, (C$_{1-16}$)alkoxy, —NHCO(C$_{1-16}$)alkyl, —NHSO$_2$(C$_{1-16}$)alkyl or —CO$_2$(C$_{1-16}$)alkyl.

5. A process for developing an image in a photographic element comprising a support and a silver halide emulsion containing an imagewise distribution of developable silver halide grains, said process comprising the step of developing said element with a silver halide color developing agent in the presence of a dye-forming coupler having the structure:

COUP—CHR—S$_e$ wherein
COUP is a dye-forming coupler moiety substituted in its coupling position with the remainder of the structure,
R is hydrogen, (C$_{1-6}$)alkyl or unsubstituted or substituted (C$_{6-15}$)aryl, and
S$_e$ is represented by the formula —L—NHSO$_2$—R$_1$
in which
L is a single bond, —(—CH$_3$=CR$_4$—)$_n$—, n is 1 or 2,
B denotes atoms sufficient to complete a 5- or 6-member ring, wherein said atoms are selected from the group of C, N, O and S,
R$_1$ is (C$_{1-20}$)alkyl, unsubstituted or substituted (C$_{6-25}$)aryl, or —CO$_2$R$_2$,
R$_2$ is H, (C$_{1-20}$)alkyl or (C$_{6-25}$)aryl, and
R$_3$, R$_4$ are identical or different, and each is H, Cl, F, —CN, —NO$_2$, —CF$_3$, —SCH$_3$, —SO$_2$CH$_3$, ($C_{1-16}$)alkyl, ($C_{1-16}$)alkoxy, —NHCO($C_{1-16}$)alkyl, —NHSO$_2$($C_{1-16}$)alkyl or —CO$_2$($C_{1-16}$)alkyl.

6. A process as claimed in claim 5, wherein $S_e$ is —NHSO$_2$R$_1$.

7. A process as claimed in claim 5, wherein COUP is a magenta or cyan dye-forming coupler moiety.

8. A photographic silver halide emulsion containing a dye-forming coupler having the structure:

COUP—CHR—S$_e$ wherein
COUP is a dye-forming coupler moiety substituted in its coupling position with the remainder of the structure,
R is hydrogen, ($C_{1-6}$)alkyl or unsubstituted or substituted ($C_{6-15}$)aryl, and
$S_e$ is represented by the formula

—L—NHSO$_2$—R$_1$ in which
L is a single bond, —(—CR$_3$=CR$_4$—)$_n$—,

,

,

, n is 1 or 2,
B denotes atoms sufficient to complete a 50 or 6-member ring, wherein said atoms are selected from the group of C, N, O and S,
R$_1$ is ($C_{1-20}$)alkyl, unsubstituted or substituted ($C_{6-25}$)aryl, or —CO$_2$R$_2$,
R$_2$ is H, ($C_{1-20}$)alkyl or ($C_{6-25}$)aryl, and
R$_3$R$_4$ are identical or different, and each is H, Cl, F, —CN, —NO$_2$, —CF$_3$, —SCH$_3$, —SO$_2$CH$_3$, ($C_{1-16}$)alkyl, ($C_{1-16}$)alkoxy, —NHCO($C_{1-16}$)alkyl, —NHSO$_2$($C_{1-16}$)alkyl or —CO$_2$($C_{1-16}$)alkyl.

9. A photographic silver halide emulsion as claimed in claim 8, wherein $S_e$ is —NHSO$_2$R$_1$.

10. A photographic silver halide emulsion as claimed in claim 8, wherein COUP is a magenta or cyan dye-forming coupler moiety.

11. A photographic element as claimed in claim 1, wherein R$_1$ is a perfluoralkyl group with 1-5 carbon atoms or an unsubstituted or substituted ($C_{6-25}$)aryl-CO$_2$R$_2$ group.

12. A process as claimed in claim 5, wherein R$_1$ is a perfluoralkyl group with 1-5 carbon atoms or an unsubstituted or substituted ($C_{6-25}$)aryl-CO$_2$R$_2$ group.

13. A photographic silver halide emulsion as claimed in claim 8, wherein R$_1$ is a perfluoralkyl group with 1-5 carbon atoms or an unsubstituted or substituted ($C_{6-25}$)aryl-CO$_2$R$_2$ group.

14. A photographic element as claimed in claim 4, wherein $S_e$ is —NHSO$_2$R$_1$.

15. A photographic element as claimed in claim 4, wherein COUP is a magenta or cyan dye-forming coupler moiety.

* * * * *